(12) United States Patent
Lubisch et al.

(10) Patent No.: US 6,482,832 B1
(45) Date of Patent: Nov. 19, 2002

(54) HETEROCYCLICALLY SUBSTITUTED AMIDES, THEIR PRODUCTION AND THEIR USE

(75) Inventors: Wilfried Lubisch, Heidelberg (DE);
Achim Möller, Grünstadt (DE);
Hans-Jörg Treiber, Brühl (DE);
Monika Knopp, Ludwigshafen (DE)

(73) Assignee: Abbott Laboratories, Abott Park, IL (US)

( * ) Notice: Subject to any disclaimer, the term of this patent is extended or adjusted under 35 U.S.C. 154(b) by 0 days.

(21) Appl. No.: 09/700,453

(22) PCT Filed: May 25, 1999

(86) PCT No.: PCT/EP99/03549

§ 371 (c)(1),
(2), (4) Date: Nov. 15, 2000

(87) PCT Pub. No.: WO99/61423

PCT Pub. Date: Dec. 2, 1999

(30) Foreign Application Priority Data

May 25, 1998 (DE) .......................... 198 23 245

(51) Int. Cl.[7] .................. C07D 209/14; C07D 215/06; C07D 217/04; A61K 31/40; A61K 31/495
(52) U.S. Cl. .................. 514/307; 546/144; 546/167; 514/314; 514/311
(58) Field of Search .................. 546/144, 167; 514/314, 307, 311

(56) References Cited

FOREIGN PATENT DOCUMENTS

| EP | 520 336 | 12/1992 |
|---|---|---|
| JP | 8-183771 | * 7/1996 |
| WO | 92/11850 | 7/1992 |
| WO | 92/12140 | 7/1992 |
| WO | 94/00095 | 1/1994 |
| WO | 95/00535 | 1/1995 |

OTHER PUBLICATIONS

Leung et al. Portease Inhibitors, J. Med. Chem., 43:306–341, 2000.*
XP–002118554, TIBS16, Apr. 1991, 150–153.
J.Med.Chem.1994,37,2918–2929, Harbeson.
J.Med.Chem.1993,36,3472–3480,Li et al.
XP–002058114,J.Med.Chem.1990,33,13–16.
Tet.Ltr.,vol. 29,No.28,3433–3436, 1988,Burkhart et al.

* cited by examiner

Primary Examiner—Mukund J. Shah
Assistant Examiner—Hong Liu
(74) Attorney, Agent, or Firm—Keil & Weinkauf

(57) ABSTRACT

Amides of the general formula I

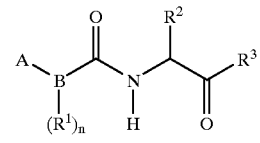

and their tautomeric and isomeric forms, possible enantiomeric and diastereomeric forms, and also possible physiologically tolerated salts, in which the variables have the meanings indicated in the description.

18 Claims, No Drawings

HETEROCYCLICALLY SUBSTITUTED AMIDES, THEIR PRODUCTION AND THEIR USE

The present invention relates to novel amides which are inhibitors of enzymes, in particular cysteine proteases, such as calpain (=calcium-dependent cysteine proteases) and its isoenzymes and cathepsins, for example cathepsins B and L. Calpains are intracellular, proteolytic enzymes from the cysteine protease group and are found in many cells. Calpains are activated by an elevated calcium concentration, with a distinction being made between calpain I or $\mu$ calpain, which is activated by $\mu$ molar concentrations of calcium ions, and calpain II or m calpain, which is activated by m molar concentrations of calcium ions (P. Johnson, Int. J. Biochem. 1990, 22(8), 811–22). Further calpain isoenzymes are nowadays being postulated (K. Suzuki et al., Biol. Chem. Hoppe-Seyler, 1995, 376(9),523–9).

Calpains are presumed to play an important role in a variety of physiological processes. These include the cleavage of regulatory proteins such as protein kinase C, cytoskeletal proteins such as MAP 2 and spectrin, muscle proteins, protein degradation in rheumatoid arthritis, proteins involved in the activation of platelets, neuropeptide metabolism, proteins in mitosis and other proteins which are listed in M. J. Barrett et al., Life Sci. 1991, 48, 1659–69 and K. K. Wang et al. and Trends in Pharmacol. Sci., 1994, 15, 412–9.

Elevated levels of calpain have been measured in a variety of pathophysiological processes, for example: ischemias of the heart (e.g. cardiac infarction), of the kidney or of the central nervous system (e.g. stroke), inflammations, muscular dystrophies, cataracts of the eyes, injuries to the central nervous system (e.g. trauma), Alzheimer's disease, etc. (see K. K. Wang, above). It is assumed that there is a connection between these diseases and persistently elevated intracellular calcium levels. These levels result in calcium-dependent processes becoming hyperactivated and no longer being subject to physiological control. Correspondingly, hyperactivation of calpains can also induce other pathophysiological processes.

It has therefore been postulated that inhibitors of the calpain enzymes could be useful for treating these diseases. This is confirmed by a variety of investigations. Thus, Seung-Chyul Hong et al., Stroke 1994, 25(3), 663–9 and R. T. Bartus et al., Neurological Res. 1995, 17, 249–58 have demonstrated that calpain inhibitors have a neuroprotective effect in acute neurodegenerative disturbances or ischemias which occur after a stroke. In the same way, following experimental brain traumas, calpain inhibitors improved recovery of the memory performance deficits and neuromotor disturbances which had occurred (K. E. Saatman et al. Proc. Natl. Acad. Sci. USA, 1996, 93,3428–3433). C. L. Edelstein et al., Proc. Natl. Acad. Sci. USA, 1995, 92, 7662–6, found calpain inhibitors to have a protective effect on kidneys damaged by hypoxia. Yoshida, Ken Ischi et al., Jap. Circ. J. 1995, 59(1), 40–8, demonstrated calpain inhibitors to have favorable effects following cardiac damage produced by ischemia or reperfusion. Since calpain inhibitors inhibit the release of β-AP4 protein, it has been proposed that they could have a potential use as therapeutic agents in Alzheimer's disease (J. Higaki et al., Neuron, 1995, 14, 651–59). Calpain inhibitors also inhibit the release of interleukin-la (N. Watanabe et al., Cytokine 1994, 6(6), 597–601). Furthermore, it has been found that calpain inhibitors have cytotoxic effects on tumor cells (E. Shiba et al. 20th Meeting Int. Ass. Breast Cancer Res., Sendai Jp, 1994, 25.–28. Sept., Int. J. Oncol. 5(Suppl.), 1994, 381).

Other possible uses of calpain inhibitors are listed in K. K. Wang, Trends in Pharmacol. Sci., 1994, 15, 412–8.

Calpain inhibitors have already been described in the literature. However, those which have been described are predominantly either irreversible inhibitors or peptide inhibitors. As a rule, irreversible inhibitors are alkylating substances and suffer from the disadvantage that they either react nonselectively in the organism or are unstable. Thus, these inhibitors often exhibit undesirable side effects, such as toxicity, and, as a consequence, are of restricted use or cannot be used at all. Examples of irreversible inhibitors which can be mentioned are the E 64 epoxides (E. B. McGowan et al., Biochem. Biophys. Res. Commun. 1989, 158, 432–5), α-halogenoketones (H. Angliker et al., J. Med. Chem. 1992, 35, 216–20) or disulfides (R. Matsueda et al., Chem. Lett. 1990, 191–194).

Many known reversible inhibitors of cysteine proteases such as calpain are peptide aldehydes, in particular dipeptide and tripeptide aldehydes such as, for example, Z-Val-Phe-H (MDL 28170) (S. Mehdi, Tends in Biol. Sci. 1991, 16, 150–3). Under physiological conditions, peptide aldehydes suffer from the disadvantage that, because of their high degree of reactivity, they are frequently unstable, can be metabolized rapidly and have a tendency to participate in nonspecific reactions which can be the cause of toxic effects (J. A. Fehrentz and B. Castro, Synthesis 1983, 676–78.

JP 08183771 (CA 1996, 605307) and EP 520336 describe aldehydes which are derived from piperidin-4-ylcarboxamides and 1-carbonylpiperidin-4-ylcarboxamides and which are calpain inhibitors. However, the aldehydes which are claimed in this present document, and which are derived from heteroaromatically substituted amides of the general structure I, have not been described previously.

Peptide ketone derivatives are also inhibitors of cysteine proteases, in particular calpains. For example, ketone derivatives in which the keto group is activated by an electrophilic group such as $CF_3$ are known to be inhibitors of serine proteases. Derivatives which contain ketones which are activated by $CF_3$ or similar groups are not particularly active, or are not active at all, in the case of cysteine proteases (M. R. Angelastro et al., J. Med. Chem. 1990, 33, 11–13). Surprisingly, the only ketone derivatives which have so far been found to be effective inhibitors of calpain are those in which, on the one hand, leaving groups in the a position cause an irreversible inhibition and, on the other hand, a carboxylic acid derivative activates the keto group (see M. R. Angelastro et al., see above; WO 92/11850; WO 92/12140; WO 94/00095 and WO 95/00535). However, only peptide derivatives of these ketoamides and ketoesters have so far been reported to be effective (Zhaozhao Li et al., J. Med. Chem. 1993, 36, 3472–80; S. L. Harbenson et al., J. Med. Chem. 1994, 37, 2918–29 and see M. R. Angelastro et al., see above).

Ketobenzamides have already been disclosed in the literature. Thus, the ketoester PhCO—Abu—COOCH$_2$CH$_3$ has been described in WO 91/09801, WO 94/00095 and WO 92/11850. However, in M. R. Angelastro et al., J. Med. Chem. 1990, 33, 11–13, the analogous phenyl derivative Ph—CONH—CH(CH$_2$Ph)—CO—COCOOCH$_3$ was found to be only a weak calpain inhibitor. This derivative is also described in J. P. Burkhardt, Tetrahedron Lett., 1988, 3433–36. However, the importance of the substituted benzamides has thus far never been investigated.

In a number of therapies such as stroke, the active compounds are administered intravenously, for example as an infusion solution. For this, it is necessary to have available substances, in this case calpain inhibitors, which are sufficiently water-soluble to enable an infusion solution to be prepared. However, many of the calpain inhibitors which have been described suffer from the disadvantage that they are only sparingly soluble or insoluble in water and consequently not suitable for intravenous administration. Active compounds of this nature can only be administered using auxiliary substances whose purpose is to mediate solubility in water (cf. R. T. Bartus et al. *J. Cereb. Blood Flow Metab.* 1994, 14, 537–544). However, these auxiliary substances, such as polyethylene glycol, frequently have attendant effects or cannot in fact be tolerated. It would consequently be a great advantage to have available a nonpeptide calpain inhibitor which is soluble in water in the absence of auxiliary substances. Such an inhibitor has not previously been described and would therefore be novel.

Substituted, nonpeptide aldehydes, ketocarboxylic esters and ketoamide derivatives are described in the present invention. These compounds are novel and surprisingly demonstrate the possibility of obtaining potent nonpeptide inhibitors of cysteine proteases, such as calpain, by incorporating rigid structural fragments. Furthermore, salt bonds with acids are possible in the case of the present compounds of the general formula I, which compounds all carry at least one aliphatic amine radical. A large number of these substances are able to exhibit solubility in water, as a 0.5% solution, at pH=4–5 and, as a result, have the desired profile for an intravenous administration as required, for example, in the case of stroke therapy.

The present invention relates to amides of the general formula I

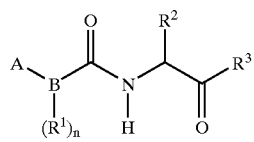

and their tautomeric and isomeric forms, possible enantiomeric and diastereomeric forms, and also possible physiologically tolerated salts, in which the variables have the following meanings:

A denotes fused rings such as

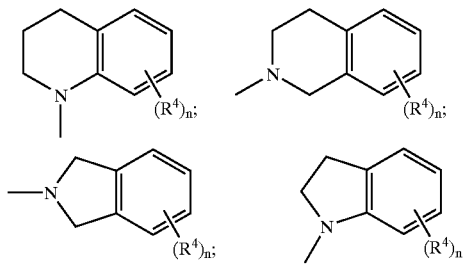

B is phenyl, naphthyl, pyridyl, pyrimidyl, pyrazyl, pyridazyl, quinolyl, quinazyl, quinoxalyl, thienyl, benzothienyl, benzofuranyl, furanyl and indolyl, and $R^1$ is hydrogen, $C_1$–$C_6$-alkyl which is branched or unbranched, O—$C_1$–$C_6$-alkyl which is branched or unbranched, $C_2$–$C_6$-alkenyl, $C_2$–$C_6$-alkynyl, $C_1$–$C_6$-alkylphenyl, $C_2$–$C_6$-alkenylphenyl, $C_2$–$C_6$-alkynylphenyl, OH, Cl, F, Br, I, $CF_3$, $NO_2$, $NH_2$, CN, COOH, COO—$C_1$–$C_4$-alkyl, NHCO—$C_1$–$C_4$-alkyl, NHCO-phenyl, $CONHR^{11}$, $NHSO_2$—$C_1$–$C_4$-alkyl, $NHSO_2$-phenyl, $SO_2$—$C_1$–$C_4$-alkyl and $SO_2$-phenyl, and $R^2$ is $C_1$–$C_6$-alkyl which is branched or unbranched and which can additionally carry a phenyl, cyclohexyl, pyridyl, thienyl, indolyl or naphthyl ring which, for its part, is substituted by a maximum of two $R^1$ radicals, and $R^3$ is hydrogen, $COOR^5$ and CO—Z, in which Z is $NR^6R^7$ and

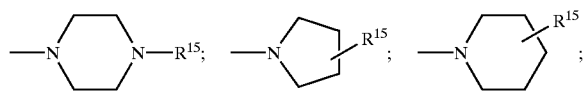

and $R^4$ is hydrogen or $(CH_2)_m NR^8R^9$, $O(CH_2)_m NR^8R^9$ or

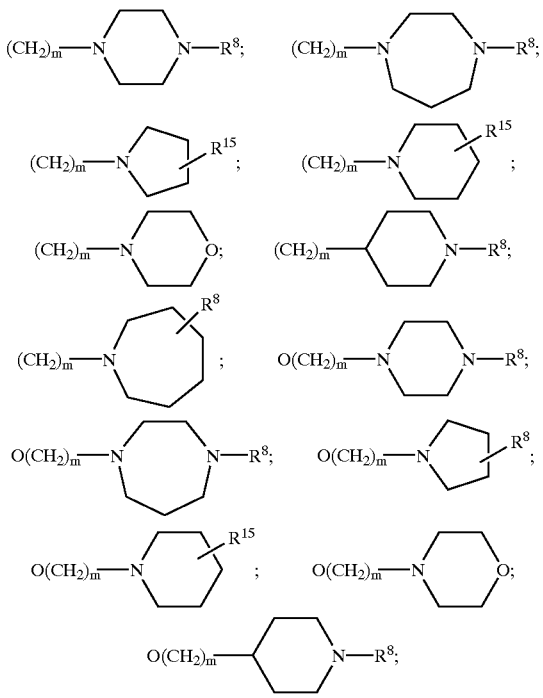

and $R^5$ is $C_1$–$C_6$-alkyl which is straight-chain or branched and which can be substituted by a phenyl ring which can itself be additionally substituted by one or two $R^{10}$ radicals, and $R^6$ is hydrogen or $C_1$–$C_6$-alkyl which is branched or unbranched, and $R^7$ is hydrogen or $C_1$–$C_6$-alkyl which is branched or unbranched and which can additionally be substituted by a phenyl or pyridine ring, which can additionally carry an $R^{10}$ radical, or by

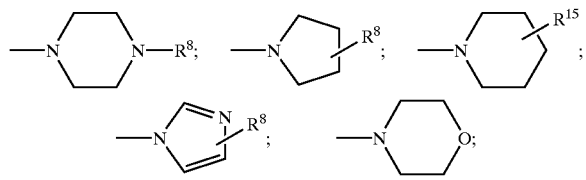

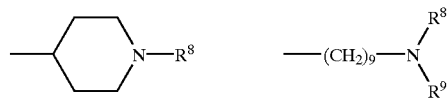

and $R^8$ is $C_1$–$C_6$-alkyl which is straight-chain or branched and which can be substituted by a phenyl ring which can itself be additionally substituted by one or two $R^{10}$ radicals, and $R^9$ is $C_1$–$C_6$-alkyl which is straight-chain or branched and which of can be substituted by a phenyl ring which can itself be additionally substituted by one or two $R^{10}$ radicals, and $R^{10}$ can be hydrogen, $C_1$–$C_4$-alkyl which is branched or unbranched, —O—$C_1$–$C_4$-alkyl, OH, Cl, F, Br, I, $CF_3$, $NO_2$, $NH_2$, CN, $CONH_2$, COOH, COO—$C_1$–$C_4$-alkyl, —NHCO–$C_1$–$C_4$-alkyl, —NHCO-phenyl, —$NHSO_2$-$C_1$–$C_4$-alkyl, —$NHSO_2$-phenyl, —$SO_2$-$C_1$–$C_4$-alkyl and —$SO_2$-phenyl, $R^{11}$ is hydrogen, $C_1$–$C_6$-alkyl which is branched or unbranched, $R^{15}$ is hydrogen or has the meaning of $R^8$, m is a number 1, 2, 3, 4, 5 or 6, and n is a number 0, 1 or 2, and o is a number 0, 1, 2, 3 or 4.

The compounds of the formula I can be employed as racemates, as enantiomerically pure compounds or as diastereomers. If enantiomerically pure compounds are desired, they can be obtained, for example, by carrying out a classical racemate resolution with the compounds of the formula I or their intermediates using a suitable optically active base or acid. On the other hand, the enantiomeric compounds can also be prepared by using commercially available compounds, for example optically active amino acids such as phenylalanine, tryptophan and tyrosine.

The present invention also relates to compounds which are mesomeric or tautomeric in relation to compounds of the formula I, for example those compounds in which the aldehyde or keto group of the formula I is present as an enol tautomer.

The present invention furthermore relates to the physiologically tolerated salts of the compounds I, which salts can be obtained by reacting compounds I with a suitable acid or base. Examples of suitable acids and bases are listed in Fortschritte der Arzneimittelforschung [Advances in Drug Research], 1966, Birkhauser Verlag, Vol. 10, pp. 224–285. They include, for example, hydrochloric acid, citric acid, tartaric acid, lactic acid, phosphoric acid, methanesulfonic acid, acetic acid, formic acid, maleic acid, fumaric acid etc., and sodium hydroxide, lithium hydroxide and potassium hydroxide, respectively.

The amides I according to the invention can be prepared in a variety of ways which have been outlined in synthesis scheme 1.

Synthesis scheme 1

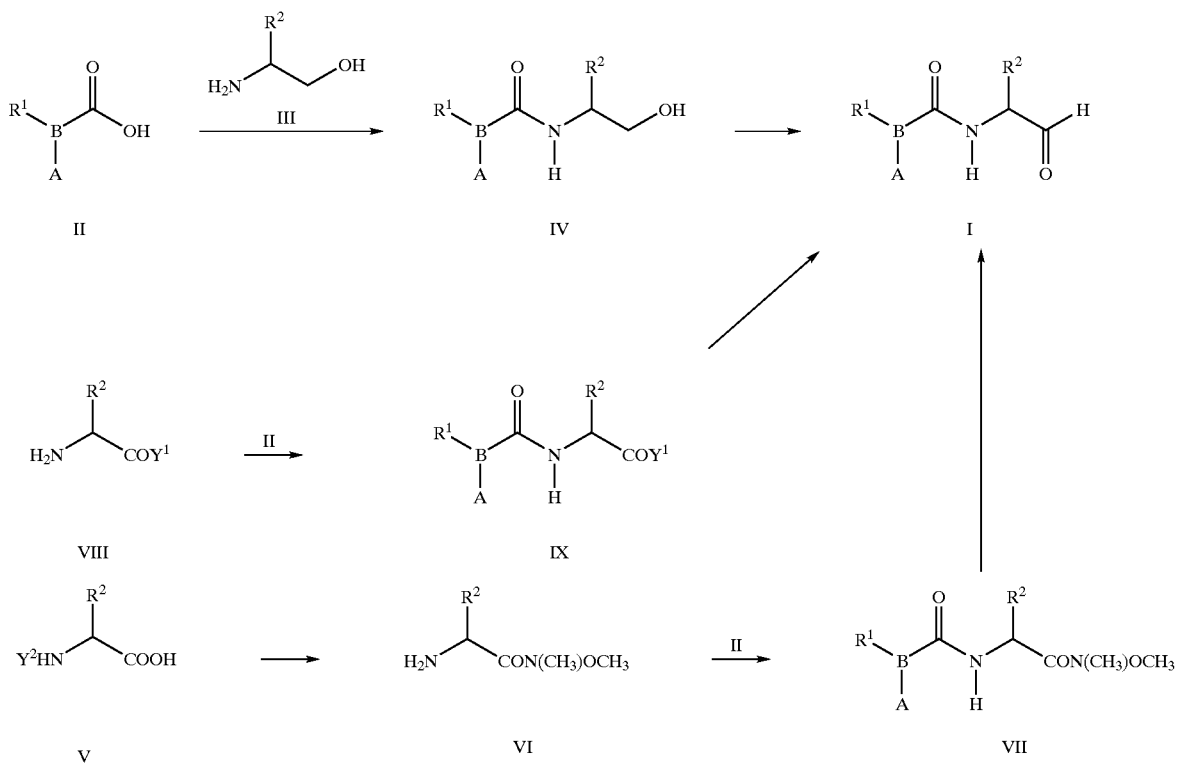

Carboxylic acids II are linked to suitable amino alcohols III in order to form the corresponding amides IV. Customary peptide coupling methods, which are cited either in C. R. Larock, Comprehensive Organic Transformations, VCH Publisher, 1989, pages 972 ff. or in Houben-Weyl, Methoden der organischen Chemie [Methods of Organic Chemistry], 4$^{th}$ Edition, E5, Chap. V, are used for this reaction. Preference is given to using "activated" acid derivatives of II, with the acid group COOH being converted into a COL group. L is a leaving group such as, for example, Cl, imidazole and N-hydroxybenzotriazole. This activated acid is then reacted with amines to give the amides IV. The reaction takes place in anhydrous, inert solvents such as methylene chloride, tetrahydrofuran and dimethylformamide at temperatures of from −20 to +25° C.

These alcohol derivatives IV can be oxidized to give the aldehyde derivatives I in accordance with the invention. Various customary oxidation reactions (see C. R. Larock, Comprehensive Organic Transformations, VCH Publisher, 1989, pages 604 ff.) such as Swern oxidations and Swern-analogous oxidations (T. T. Tidwell, Synthesis 1990, 857–70), sodium hypochloride [sic]/TEMPO (S. L. Harbenson et al., see above) or Dess-Martin (J. Org. Chem. 1983, 48, 4155) can be used for this purpose. Preference is given to carrying out this reaction in inert, aprotic solvents such as dimethylformamide, tetrahydrofuran or methylene chloride containing oxidizing agents such as $DMSO/pyxSO_3$ or $DMSO$/oxalyl chloride at temperatures of from −50 to +25° C., depending on the method (see the above literature).

Alternatively, the carboxylic acid II can be reacted with aminohydroxamic derivatives VI to form benzamides VII. The reaction is then conducted in the same way as when preparing IV. The hydroxamic derivatives VI can be obtained from the protected amino acids V by reacting them with a hydroxylamine. The amide preparation method which has already been described is used in this case as well. The protecting group $Y^2$, for example Boc, is eliminated in a customary manner, for example using trifluoroacetic acid. The resulting amidohydroxamic acids VII can be converted by reduction into the aldehydes I according to the invention. For this, lithium aluminum hydride is, for example, used as the reducing agent, at temperatures of from −60 to 0° C. and in inert solvents such as tetrahydrofuran or ether.

In analogy with the latter method, it is also possible to prepare carboxylic acids or acid derivatives, such as esters IX ($Y^1$=OR', SR') which can likewise be converted by reduction into the aldehydes I according to the invention. These methods are cited in C. R. Larock, Comprehensive Organic Transformations, VCH Publisher, 1989, pages 619–26.

The novel heterocyclically substituted amides I which carry a ketoamide or ketoester group can be prepared in a variety of ways which have been outlined in synthesis schemes 2 and 3.

Where appropriate, the carboxylic esters IIa are converted into the acids II using acids or bases, such as lithium hydroxide, sodium hydroxide or potassium hydroxide, in an aqueous medium or in mixtures consisting of water and organic solvents such as alcohols and tetrahydrofuran, and at room temperature or elevated temperatures, such as 25–100° C.

These acids II are linked to an α-amino acid derivative using customary conditions which are listed, for example, in Houben-Weyl, Methoden der organischen Chemie [Methods in organic Chemistry], $4^{th}$ Ed., E5, Chap. V, and C. R. Larock, Comprehensive Organic Transformations, VCH Publisher, 1989, Ch.9.

For example, the carboxylic acids II are converted into the "activated" acid derivatives IIb=Y-COL, with L being a leaving group such as Cl, imidazole and N-hydroxybenzotriazole, with these activated acid derivatives subsequently being converted into the derivative XI by adding an amino acid derivative $H_2N$—$CH(R^2)$—COOR. This reaction takes place in anhydrous, inert solvents such as methylene chloride, tetrahydrofuran and dimethylformamide, at temperatures of from −20 to +25° C.

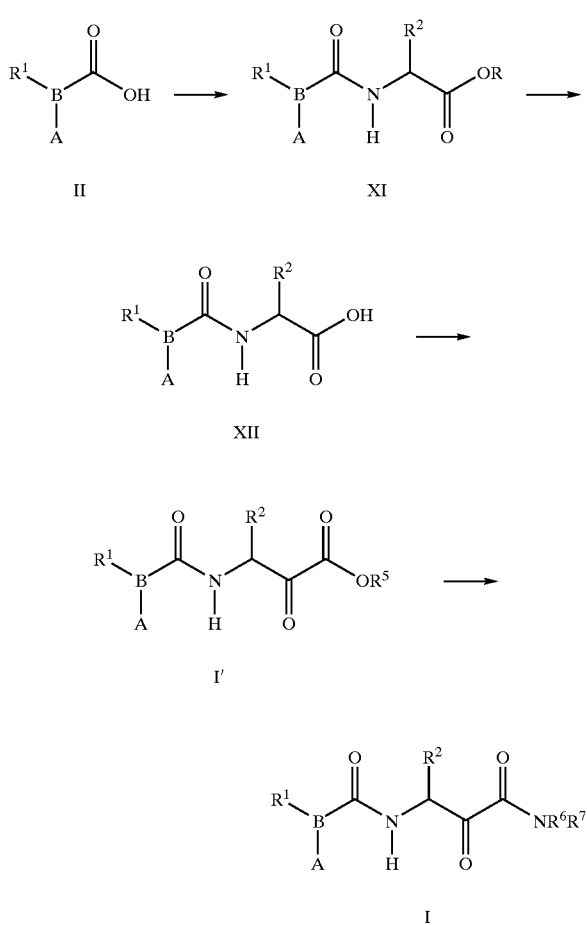

The derivatives XI, which are as a rule esters, are converted into the ketocarboxylic acids XII in analogy with the above-described hydrolysis. The ketoesters I' are prepared in a reaction analogous to a Dakin-West reaction, with a method of Zhaozhao Li et al., J. Med. Chem., 1993, 36, 3472–80 being used. In this method, carboxylic acids such as XII are reacted, at elevated temperature (50–100° C.) and in solvents such as tetrahydrofuran, with oxalic acid monoester chloride and the resulting product is then reacted with bases, such as sodium ethoxide, in ethanol and at temperatures of 25–80° C., to give the ketoester I' in accordance with the invention. The ketoesters I' can, for example, be hydrolyzed, as described above, to give ketocarboxylic acids according to the invention.

The conversion into ketobenzamides I also takes place in analogy with the method of Zhaozhao Li et al. (see above). The keto group in I' is protected by adding 1,2-ethanedithiol and using a Lewis acid catalyst, for example boron trifluoride etherate, in inert solvents such as methylene chloride and at room temperature, with a dithiane being formed. These derivatives are reacted with amines in polar solvents, such as alcohols, at temperatures of 0–80° C., resulting in the formation of the ketoamides I ($R^3$=$CONR^6R^7$).

Synthesis scheme 3

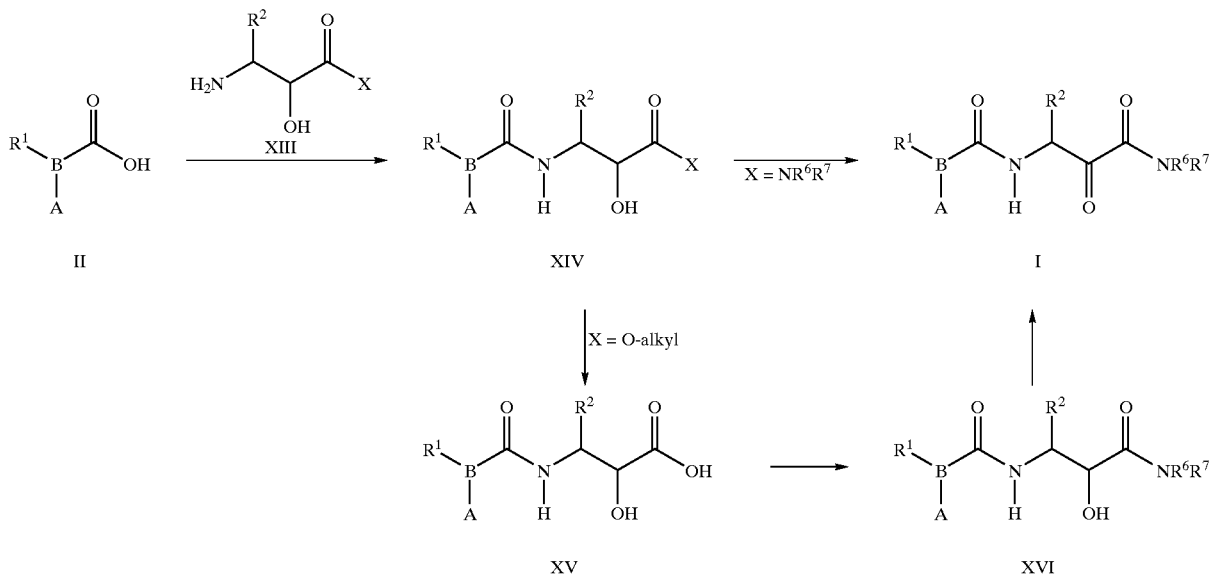

An alternative method is depicted in scheme 3. The ketocarboxylic acids II are reacted with aminohydroxycarboxylic acid derivatives XIII (for the preparation of XIII, see S. L. Harbenson et al., J. Med. Chem. 1994, 37, 2918–29 or J. P. Burkhardt et al. Tetrahedron Lett. 1988, 29, 3433–3436), using customary peptide coupling methods (see above, Houben-Weyl), with amides XIV being formed. These alcohol derivatives XIV can be oxidized to give the ketocarboxylic acid derivatives I according to the invention. A variety of customary oxidation reactions (see C. R. Larock, Comprehensive Organic Transformations, VCH Publisher, 1989, pages 604 ff.) such as, for example, Swern oxidations and Swern-analogous oxidations, preferably a dimethyl sulfoxide/pyridine-sulfur trioxide complex in solvents such as methylene chloride or tetrahydrofuran, where appropriate with the addition of dimethyl sulfoxide, at room temperature or at temperatures of from −50 to 25° C., (T. T. Tidwell, Synthesis 1990, 857–70) or sodium hypochloride [sic]/TEMPO (S. L. Harbenson et al., see above), can be used for this purpose.

When XIV are α-hydroxy esters (X=O-alkyl), these esters can then be hydrolyzed to give carboxylic acids XV using methods which are analogous to the above, preferably, however, using lithium hydroxide in water/tetrahydrofuran mixtures at room temperature. Other esters or amides XVI are prepared by reacting alcohols or amines under coupling conditions which have already been described. The alcohol derivatives XVI can once again be oxidized to give the ketocarboxylic acid derivatives I according to the invention.

The preparation of some of the carboxylic esters II has already been described; others are prepared using customary chemical methods.

The A-B bond is formed by reacting the halogenoaromatic compounds with the corresponding amines in the presence of potassium carbonate and 18-crown-6 in DMF, THF or BuOH. The dialkylaminoalkyl substituents are obtained by reductive amination of the aldehyde derivatives with the corresponding amines in the presence of boron hydrides, such as a $BH_3$-pyridine complex or $NaBH_3CN$ (A. F. Abdel-Magid, C. A. Maryanoff, K. G. Carson, Tetrahedron Lett. 10990, 31, 5595; A. E. Moormann, Synth. Commun. 1993, 23, 789).

The heterocyclically substituted amides I which are contained in the present invention are inhibitors of cysteine proteases, in particular cysteine proteases such as calpains I and II and cathepsins B and L.

The inhibitory effect of the heterocyclically substituted amides I was ascertained using enzyme tests which are customary in the literature, with the concentration of the inhibitor at which 50% of the enzyme activity is inhibited ($IC_{50}$) being determined as the criterion of efficacy. This assessment was used to measure the inhibitory effect of the amide I on calpain I, calpain II and cathepsin B.

Cathepsin B Test

The inhibition of cathepsin B was determined using an analogous method to that described by S. Hasnain et al., J. Biol. Chem. 1993, 268, 235–40.

2 μL of an inhibitor solution prepared from inhibitor and DMSO (final concentrations: 100 μM to 0.01 μM) are added to 88 μL of cathepsin B (human liver cathepsin B (Calbiochem), diluted to 5 units in 500 μM buffer). This mixture is pre-incubated at room temperature (25° C.) for 60 minutes and the reaction is then started by adding 10 μL of 10 mM Z-Arg-Arg-pNA (in buffer containing 10% DMSO). The reaction is monitored for 30 minutes in a microtiter plate reader at 405 nM [sic]. The $IC_{50}$'s are then determined from the maximum slopes.

Calpain I and Calpain II Test

The inhibitory properties of calpain inhibitors are tested in buffer having the composition 50 mM tris-HCl, pH 7.5; 0.1 M NaCl; 1 mM dithiothreitol; 0.11 mM $CaCl_2$, and using the fluorogenic calpain substrate Suc-Leu-Tyr-AMC (25 mM dissolved in DMSO, Bachem/Switzerland). Human μ calpain is isolated from erythrocytes, with an enzyme having a purity of >95%, as assessed by SDS-PAGE, Western blot analysis and N-terminal sequencing, being obtained after several chromatographic steps (DEAE Sepharose, Phenyl Sepharose, Superdex 200 and Blue Sepharose). The fluorescence of the cleavage product 7-amino-4-methylcoumarin (AMC) is monitored in a Spex-Fluorolog Fluorimeter at λex=380 nm and λem=460 nm. The cleavage of the substrate is linear over a measuring period of 60 min and the autocatalytic activity of calpain is low if the experiments are carried out at a temperature of 12° C. The inhibitors and the calpain substrate are added to the assay in the form of solutions in DMSO, in association with which the final concentration of DMSO should not exceed 2%.

In one assay, 10 μl of substrate (final concentration 250 μM) and then 10 μl of μ calpain (final concentration 2 μg/ml, i.e. 18 nM) are added to a 1 ml cuvette containing buffer. The calpain-mediated cleavage of the substrate is measured for 15–20 min. 10 μl of inhibitor (50–100 μM solution in DMSO) are then added and inhibition of the cleavage is measured for a further 40 min.

$K_i$ values are determined using the classical equation for reversible inhibition:

(Methods in Enzymology) Ki=I/(v0/vi)−1; where I=inhibitor concentration, v0=initial velocity before adding the inhibitor; vi=reaction velocity at equilibrium.

The velocity is calculated from v=release of AMC/time, i.e. intensity/time.

Calpain is an intracellular cysteine protease. Calpain inhibitors have to be able to pass through the cell membrane in order to prevent calpain degrading intracellular proteins. Some known calpain inhibitors, for example E 64 and leupeptin, are only able to surmount the cell membrane with difficulty and consequently only have a poor effect on cells even though they are good calpain inhibitors. The aim is to find compounds which are better able to traverse the membrane. We use human platelets to demonstrate the membrane-traversing ability of calpain inhibitors.

Calpain-mediated degradation of tyrosine kinase pp60src in platelets

After platelet activation, the tyrosine kinase pp60src is cleaved by calpain. This has been investigated in detail by Oda et al. in J. Biol. Chem., 1993, Vol. 268, 12603–12608. In this connection, it was shown that calpeptin, which is an inhibitor of calpain, can prevent the cleavage of pp60src. The cellular efficacy of our substances was tested following the method used in this publication. Fresh human, citrate-treated blood was centrifuged at 200 g for 15 min. The platelet-rich plasma was pooled and diluted 1:1 with platelet buffer (platelet buffer: 68 mM NaCl, 2.7 mM KCl, 0.5 MM $MgCl_2 \times 6\ H_2O$, 0.24 mM $NaH_2PO_4 \times H_2O$, 12 mM $NaHCO_3$, 5.6 mM glucose, 1 mM EDTA, pH 7.4). After a centrifugation and washing step using platelet buffer, the platelets were adjusted to a concentration of $10^7$ cells/ml. The human platelets were isolated at RT.

In the test assay, isolated platelets ($2 \times 10^6$) were preincubated, at 37° C. for 5 min, with different concentrations of inhibitors (dissolved in DMSO). The platelets were then activated with 1 μM ionophore A23187 and 5 mM $CaCl_2$. After incubating for 5 min, the platelets were centrifuged briefly at 13000 rpm and the pellet was taken up in SDS sample buffer (SDS sample buffer: 20 mM tris-HCl, 5 mM EDTA, 5 mM EGTA, 1 mM DTT, 0.5 mM PMSF, 5 μg of leupeptin/ml, 10 μg of pepstatin/ml, 10% glycerol and 1% SDS). The proteins were fractionated in a 12% gel and pp60src and its 52 kDa and 47 kDa cleavage products were identified by Western blotting. The polyclonal rabbit anti-Cys-src ($pp60^{c-src}$) antibody was obtained from Biomol Feinchemikalien (Hamburg). This primary antibody was detected with a goat HRP-coupled second antibody (Boehringer Mannheim, FRG). The western blotting was carried out using known methods.

The cleavage of pp60src was quantified densitometrically with the controls employed being nonactivated platelets (control 1: no cleavage) and ionophore-treated and calcium-treated platelets (control 2: corresponds to 100% cleavage).

The $ED_{50}$ value is the concentration of inhibitor at which the intensity of the color reaction is reduced by 50%.

Glutamate-induced Cell Death in Cortical Neurones

The test was carried out as described in Choi D. W., Maulucci-Gedde M. A. and Kriegstein A. R., "Glutamate neurotoxicity in cortical cell culture". J. Neurosci. 1989, 7, 357–368.

The two halves of the cortex were dissected out of 15-day-old mouse embryos and the individual cells were isolated enzymically (trypsin). These cells (glia cells and cortical neurones) are sown in 24-well plates. After three days (laminin-coated plates) or seven days (ornithine-coated plattes), mitosis treatment is carried out using FDU (5-fluoro-2-deoxyuridine). 15 days after preparing the cells, cell death is induced by adding glutamate (15 minutes). The calpain inhibitors are added after the glutamate has been removed. 24 hours later, cell damage is ascertained by measuring lactate dehydrogenase (LDH) in the cell culture supernatant.

It is postulated that calpain also plays a role in apoptotic cell death (M. K. T. Squier et al. J. Cell. Physiol. 1994, 159, 229–237; T. Patel et al. Faseb Journal 1996, 590, 587–597). Cell death was therefore induced with calcium in the presence of a calcium ionophore in another model represented by a human cell line. Calpain inhibitors have to penetrate into the cell, and then inhibit calpain in the cell, in order to prevent the cell death which has been induced.

Calcium-mediated Cell Death in NT2 Cells

In the human cell line NT2, cell death can be induced by calcium in the presence of the ionophore A23187. 20 hours before the experiment, cells were plated out in microtiter plates at the rate of $10^5$ cells/well. After this time had elapsed, the cells were incubated with various concentrations of inhibitor in the presence of 2.5 μM ionophore and 5 mM calcium. After 5 hours, 0.05 ml of XTT (Cell Proliferation Kit II, Boehringer Mannheim) was added to the reaction mixture. The optical density is measured approximately 17 hours later, in accordance with the manufacturer's instructions, in an SLT Easy Reader EAR 400. The optical density at which half the cells have died is calculated from the two controls containing cells without inhibitors, with these cells being incubated either in the absence or in the presence of ionophore.

Increased activities of glutamate, which lead to states of superexcitation or toxic effects in the central nervous system (CNS), occur in a number of neurological diseases or psychic disturbances. Glutamate mediates its effects by way of a variety of receptors. Two of these receptors are termed the NMDA receptor and the AMPA receptor, respectively, after their specific agonists. It is consequently possible to employ antagonists to these glutamate-mediated effects for treating these diseases, in particular for therapeutic use against neurodegenerative diseases such as Huntington's chorea and Parkinson's disease, and against neurotoxic disturbances following hypoxia, anoxia and ischemia and following lesions which occur after stroke and trauma, or else as antiepileptic agents (cf. Arzneim. Forschung 1990, 40, 511–514; TIPS, 1990, 11, 334–338; Drugs of the Future 1989, 14, 1059–1071).

Protection against cerebral superexcitation caused by excitatory amino acids (NMDA antagonism and AMPA antagonism in the mouse).

Intracerebral administration of excitatory amino acids EAA (Excitatory Amino Acids) induces a superexcitation which is so massive that it leads in a short time to convulsions and to the death of the animals (mice). These symptoms can be inhibited by the systemic, e.g. intraperitoneal, administration of active compounds (EAA antagonists) which act on the central nervous system. Since excessive activation of EAA receptors in the central nervous system plays an important role in the pathogenesis of a variety of neurological diseases, the EAA antagonism which has been demonstrated in vivo suggests that it might be possible to use the substances in the therapy of these CNS diseases. The efficacy of the substances was measured by determining the $ED_{50}$ value, at which the prior i.p. administration of the substance being measured results in 50% of the animals remaining sympton-free following the administration of a defined dose of either NMDA or AMPA.

The heterocyclically substituted amides I are inhibitors of cysteine derivatives [sic] such as calpain I and calpain II and cathepsin B and cathepsin L and can consequently be used for controlling diseases which are associated with an increased activity of the calpain or cathepsin enzymes. Accordingly, the present amides I can be used for treating neurodegenerative diseases which occur following ischemia, trauma, subarachnoidal hemorrhages and stroke, and for treating neurodegenerative diseases such as multiple infarction dementia, Alzheimer's disease and Huntington's disease, and for treating epilepsies, and, furthermore, for treating damage to the heart following cardiac ischemias, damage to the kidneys following renal ischemias, skeletal muscle damage, muscular dystrophies, damage which arises due to proliferation of the smooth muscle cells, coronary vasospasms, cerebral vasospasms, cataracts of the eyes and restenosis of the blood vessels following angioplasty. Furthermore, the amides I can be of use in the chemotherapy of tumors and their metastases and for treating diseases in which there is an increased level of interleukin 1, as in the case of inflammations and rheumatic diseases.

The pharmaceutical preparations according to the invention contain a therapeutically effective quantity of the compounds I in addition to the customary pharmaceutical adjuvants.

For local, external use, for example in powders, ointments or sprays, the active compounds can be present in the customary concentrations. As a rule, the active compounds are present in a quantity of from 0.001 to 1% by weight, preferably from 0.001 to 0.1% by weight.

For internal use, the preparations are administered in individual doses. In an individual dose, from 0.1 to 100 mg is/are administered per kg of body weight. The preparation may be administered daily in one or more doses depending on the nature and severity of the diseases.

In addition to the active compound, the pharmaceutical preparations according to the invention contain the excipients and diluents which are customary in accordance with the desired mode of administration. Adjuvants which are customary in pharmaceutical technology, such as ethanol, isopropanol, ethoxylated castor oil, ethoxylated hydrated castor oil, polyacrylic acid, polyethylene glycol, polyethylene glycostearate, ethoxylated fatty alcohols, paraffin oil, vaseline and lanolin, can be employed for local external use. Examples of suitable adjuvants for internal use are lactose, propylene glycol, ethanol, starch, talc and polyvinylpyrrolidone.

Antioxidants such as tocopherol and butylated hydroxyanisole and also butylated hydroxytoluene, taste-improving additives, stabilizers, emulsifiers and glidants can also be present.

The substances which are present in the preparation in addition to the active compound, and also the substances which are used in producing the pharmacteutical preparations, are toxicologically harmless and compatible with the respective active compound. The pharmaceutical preparations are produced in a customary manner, for example by mixing the active compound with other customary excipients and diluents.

The pharmaceutical preparations can be administered in a variety of ways, for example perorally, parenterally, such as intravenously by means of infusion, subcutaneously, intraperitoneally and topically. Thus, possible preparation forms are tablets, emulsions, infusion solutions, injection solutions, pastes, ointments, gels, creams, lotions, powders and sprays.

EXAMPLES

Example 1

2-(1,2,3,4-Tetrahydroisoquinolin-2-yl)nicotin[N-(1-carbamoyl-1-oxo-3-phenylpropan-2-yl)]amide a) Ethyl 2-(1,2,3,4-tetrahydroisoquinolin-2-yl)nicotinate 4.0 g (19.4 mmol) of ethyl 2-chloronicotinate, together with 3.2 g (19.4 mmol) of 1,2,3,4-tetrahydroisoquinoline hydrochloride and 5.36 g of potassium carbonate were heated at 110° C. for 3 h in 50 ml of DMF while stirring. Water was then added and the whole was extracted with ether; the ether phase was then washed with ammonium chloride, dried and evaporated. The crude product was purified chromatographically (silica gel/heptane-ethyl acetate 20-1), giving a yield of 4.8 g (87%).

b) 2-(1,2,3,4-Tetrahydroisoquinolin-2-yl)nicotinic Acid 4.8 g of the intermediate 1a were hydrolyzed with 2N sodium hydroxide solution and ethanol at boiling temperature (2 h). The mixture was diluted with water and then extracted with ethyl acetate; the aqueous phase was then acidified to pH 4–5 with acetic acid. A total of 3.3 g (81%) was obtained by filtering off the resulting precipitate with suction and extracting the aqueous phase with ethyl acetate once again. M.p. 150–152° C.

c) 2-(1,2,3,4-Tetrahydroisoquinolin-2-yl)nicotin[N-(1-carbamoyl-1-ol-3-phenylpropan-2-yl)]amide 1.65 g (6.5 mmol) of the intermediate 1c [sic] were initially introduced, together with 1.0 ml (7.2 mmol) of triethylamine and 0.88 [lacuna] (6.5 mmol) of 1-hydroxy-1H-benzotriazole (HOBT), at 0° C., into 50 ml of DMF, and 1.5 g (6.5 mmol) of 3-amino-2-hydroxy-4-phenylbutyramide hydrochloride, 2.7 ml (19.5 mmol) of triethylamine and 1.37 g (7.2 mmol) of N'-(3-dimethylaminopropyl)-N-ethylcarbodiimide hydrochloride (EDC) were then added. After the mixture had been stirred overnight at room temperature, water and ether were added and the solid was filtered off with suction, giving a yield of 2.4 g (85%). M.p. 237–239° C.

d) 2-(1,2,3,4-Tetrahydroisoquinolin-2-yl)nicotin[N-(1-carbamoyl-1-oxo-3-phenylpropan-2-yl)]amide 1.3 g (3.0 mmol) of the intermediate 1c together with 1.9 ml (13.6 mmol) of triethylamine were dissolved, at 0° C., in 30 ml of DMSO and 1.92 g (12 mmol) of pyridine-SO$_3$ complex were then added. After the mixture had been stirred overnight, dil. sodium hydrogen carbonate solution was added and the whole was extracted 3 times with ethyl acetate. The combined ethyl acetate phases were evaporated after drying and the residue was stirred with methylene chloride; the solid was then filtered off with suction and dried in vacuo.

Yield: 400 mg (31% of theory) M.p. 163–165° C. $^1$H NMR (DMSO-D$_6$): δ=2.8–3.2 (6H), 4.3 (2H), 5.4 (1H), 6.8–7.5 (11H), 7.8–8.1 (3H), 9.0 (1H) ppm.

Examples 2–5 were prepared in an analogous manner.

Example 2

2-(1,2,3,4-Tetrahydro-6,7-dimethoxyisoquinolin-2-yl)nicotin[N-(1-carbamoyl-1-oxo-3-phenylpropan-2-yl)]amide M.p. 214–216° C. $^1$H NMR (DMSO-D$_6$) [sic]: δ=2.7–3.5 (6H), 3.8 (6H), 4.3 (2H), 5.5 (1H), 6.7–7.5 (9H), 7.9–8.1 (2H), 9.0 (1H) ppm.

Example 3

2-(1,2,3,4-Tetrahydro-6,7-dimethoxyisoquinolin-2-yl)nicotin[N-(1-carbamoyl-1-oxohexan-2-yl)]amide M.p. 182° C. $^1$H NMR (DMSO-D$_6$): δ=0.9–1.8 (9H), 2.8 (2H), 3.5–3.7 (8H), 4.3 (2H), 5.1 (1H), 6.7–6.9 (3H), 7.7–8.2 (4H), 9.0 (1H) ppm.

Example 4

2-(1,2,3,4-Tetrahydroisoquinolin-2-yl)benz[N-(1-carbamoyl-1-oxo-3-phenylpropan-2-yl)]amide M.p. 156–158° C. $^1$H NMR (DMSO-D$_6$): δ=2.3–3.2 (6H), 4.0–4.3 (2H), 5.3 (1H), 6.9–8.0 (15H), 10.0 (1H) ppm.

Example 5

4-(1,2,3,4-Tetrahydroisoquinolin-2-yl)nicotin[N-(1-carbamoyl-1-oxo-3-phenylpropan-2-yl)]amide M.p. 160–162° C. $^1$H NMR (DMSO-D$_6$): δ=2.7–3.5 (6H), 4.2–4.5 (2H), 5.5 (1H), 7.0–7.4 (11H), 7.9–8.1 (3H), 9.1 (1H) ppm.

Other examples are given in the following table (Examples 1–250).

| No. | (R$^1$)n—B—CO | A | R$^2$ | R$^3$ |
|---|---|---|---|---|
| 1 | 5-MeO-2-methylbenzoyl | 1,2,3,4-tetrahydroquinolin-1-yl | Bn | CONH$_2$ |
| 2 | 4,5-dimethoxy-2-methylbenzoyl | 1,2,3,4-tetrahydroisoquinolin-2-yl | Bn | H |
| 3 | 4-methylnicotinoyl | 2,3-dihydroindol-1-yl | Bn | CONH$_2$ |
| 4 | 5-MeO-2-methylbenzoyl | 2,3-dihydroisoindol-2-yl | Bn | CONH$_2$ |
| 5 | 2-methylnicotinoyl | 2-(pyrrolidin-1-ylmethyl)-2,3-dihydroindol-1-yl | nBu | CONH$_2$ |
| 6 | 2-methylnicotinoyl | 2-(piperidin-1-ylmethyl)-2,3-dihydroindol-1-yl | Bn | H |
| 7 | 2-methylnicotinoyl | 2-(dimethylaminomethyl)-2,3-dihydroindol-1-yl | nBu | CONH$_2$ |
| 8 | 2-methylnicotinoyl | 2-(diethylaminomethyl)-2,3-dihydroindol-1-yl | nBu | H |
| 9 | 3-methylpyrazin-2-ylcarbonyl | 6-methoxy-1,2,3,4-tetrahydroisoquinolin-2-yl | Bn | H |

-continued

| No. | (R¹)n—B—CO | A | R² | R³ |
|---|---|---|---|---|
| 10 | 2-methyl-pyrazine-3-carbonyl | 6,7-dimethoxy-1,2,3,4-tetrahydroisoquinolin-2-yl | Bn | H |
| 11 | 2-methyl-pyrazine-3-carbonyl | 1,2,3,4-tetrahydroquinolin-1-yl | Bn | H |
| 12 | 5-methoxy-2-methyl-benzoyl | indolin-1-yl | Bn | H |
| 13 | 2-methyl-pyridine-3-carbonyl | 7-methoxy-1,2,3,4-tetrahydroisoquinolin-2-yl | Bn | CONH$_2$ |
| 14 | 2-methyl-pyridine-3-carbonyl | 1,2,3,4-tetrahydroisoquinolin-2-yl | Bn | CONH$_2$ |
| 15 | 5-methoxy-2-methyl-benzoyl | isoindolin-2-yl | Bn | H |
| 16 | 2-methyl-pyridine-3-carbonyl | 2-(morpholin-4-ylmethyl)-indolin-1-yl | nBu | CONH$_2$ |
| 17 | 2-methyl-pyridine-3-carbonyl | 2-((4-methylpiperazin-1-yl)methyl)-1,2,3,4-tetrahydroquinolin-1-yl | CH$_2$cHex | CONH$_2$ |
| 18 | 2-methyl-pyrazine-3-carbonyl | 7-methoxy-1,2,3,4-tetrahydroisoquinolin-2-yl | Bn | CONH$_2$ |
| 19 | 2-methyl-pyridine-3-carbonyl | 6-(pyrrolidin-1-ylmethyl)-1,2,3,4-tetrahydroisoquinolin-2-yl | Bn | H |
| 20 | 2-methyl-pyridine-3-carbonyl | 6-((4-methylpiperazin-1-yl)methyl)-1,2,3,4-tetrahydroisoquinolin-2-yl | nBu | CONH$_2$ |
| 21 | 2-methyl-pyridine-3-carbonyl | indolin-1-yl | | 3-ethyl-indol-1-yl-CONH-CH$_2$CH$_2$-morpholin-4-yl |

-continued

| No. | (R¹)n—B—CO | A | R² | R³ |
|---|---|---|---|---|
| 22 | 4-methylbenzoyl | 1,2,3,4-tetrahydroisoquinolin-2-yl | Bn | H |
| 23 | 4-methylbenzoyl | 1,2,3,4-tetrahydroquinolin-1-yl | Bn | CONH$_2$ |
| 24 | 2-methylpyridine-3-carbonyl | 6-(dimethylaminomethyl)-1,2,3,4-tetrahydroisoquinolin-2-yl | nBu | H |
| 25 | 2-methylbenzoyl | 2,3-dihydro-1H-isoindol-2-yl | Bn | CONH$_2$ |
| 26 | 3-methylbenzoyl | 2,3-dihydro-1H-indol-1-yl | Bn | H |
| 27 | 2-methylbenzoyl | 6-methoxy-1,2,3,4-tetrahydroisoquinolin-2-yl | Bn | CONH$_2$ |
| 28 | 2-methylpyridine-3-carbonyl | 1,2,3,4-tetrahydroisoquinolin-2-yl | 3-ethylthiophen-2-yl | CONH$_2$ |
| 29 | 2-methylpyridine-3-carbonyl | 1,2,3,4-tetrahydroquinolin-1-yl | 3-ethylthiophen-2-yl | CONH$_2$ |
| 30 | 2-methylpyridine-3-carbonyl | 6-(diethylaminomethyl)-1,2,3,4-tetrahydroisoquinolin-2-yl | CH$_2$cHex | H |
| 31 | 2-methylpyridine-3-carbonyl | 6-(morpholin-4-ylmethyl)-1,2,3,4-tetrahydroisoquinolin-2-yl | Bn | CONH$_2$ |
| 32 | 2-methylpyridine-3-carbonyl | 6-(piperidin-1-ylmethyl)-1,2,3,4-tetrahydroisoquinolin-2-yl | Bn | H |
| 33 | 4-methylbenzoyl | 6,7-dimethoxy-1,2,3,4-tetrahydroisoquinolin-2-yl | Bn | H |

-continued

| No. | (R¹)n—B—CO | A | R² | R³ |
|---|---|---|---|---|
| 34 | 3-methylbenzoyl | 6-methoxy-1,2,3,4-tetrahydroisoquinolin-2-yl | Bn | CONH$_2$ |
| 35 | 2-methylpyridine-3-carbonyl | 1,2,3,4-tetrahydroquinolin-1-yl | pyridin-4-ylmethyl | CONH$_2$ |
| 36 | 2-methylpyridine-3-carbonyl | 1,2,3,4-tetrahydroisoquinolin-2-yl | pyridin-4-ylmethyl | H |
| 37 | 2-methylpyridine-3-carbonyl | 5-(diethylaminomethyl)-2,3-dihydro-1H-indol-1-yl | Bn | H |
| 38 | 2-methylpyridine-3-carbonyl | 6-(diethylaminomethyl)-2,3-dihydro-1H-indol-1-yl | Bn | CONH$_2$ |
| 39 | 4-methylpyridine-3-carbonyl | 1,2,3,4-tetrahydroquinolin-1-yl | 3-ethyl-1H-indol-? | CONH-CH$_2$CH$_2$-NEt$_2$ |
| 40 | 4-methylpyridine-3-carbonyl | 1,2,3,4-tetrahydroisoquinolin-2-yl | Bn | H |
| 41 | 3-methylpyrazine-2-carbonyl | 2,3-dihydro-1H-isoindol-2-yl | Bn | CONH$_2$ |
| 42 | 4,5-dimethoxy-2-methylbenzoyl | 2,3-dihydro-1H-indol-1-yl | Bn | H |
| 43 | 5-methoxy-2-methylbenzoyl | 1,2,3,4-tetrahydroquinolin-1-yl | Bn | H |
| 44 | 2-methylpyridine-3-carbonyl | 7-(diethylaminomethyl)-2,3-dihydro-1H-indol-1-yl | Bn | CONH$_2$ |
| 45 | 2-methylbenzoyl | 6,7-dimethoxy-1,2,3,4-tetrahydroisoquinolin-2-yl | Bn | H |

-continued
| No. | (R¹)n—B—CO | A | R² | R³ |
|---|---|---|---|---|
| 46 | 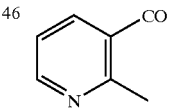 | 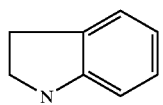 | 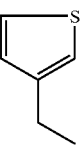 | H |
| 47 | 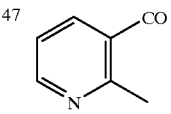 | 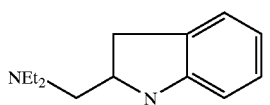 | Bn | CONH$_2$ |
| 48 | 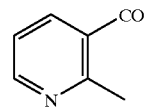 | 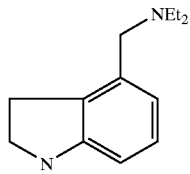 | Bn | H |
| 49 | 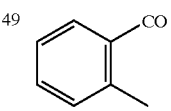 | 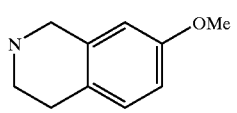 | Bn | CONH$_2$ |
| 50 | 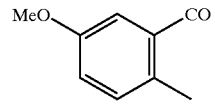 | 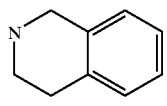 | Bn | H |
| 51 | 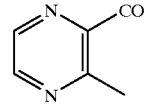 | 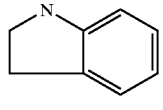 | Bn | CONH$_2$ |
| 52 | 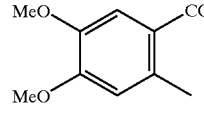 | 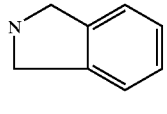 | Bn | H |
| 53 | 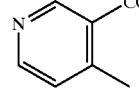 | 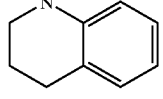 | Bn | CONH$_2$ |
| 54 | 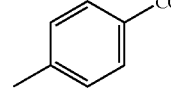 | 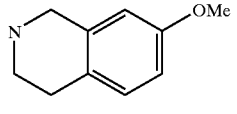 | Bn | H |
| 55 | 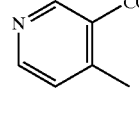 | 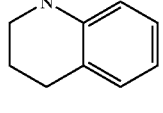 | 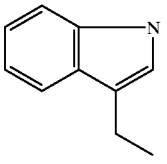 | |
| 56 | 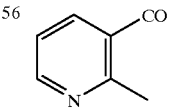 | 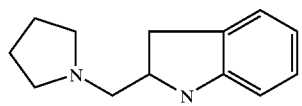 | CH$_2$cHex | H |

-continued

| No. | (R¹)n—B—CO | A | R² | R³ |
|---|---|---|---|---|
| 57 | 2-methylpyridine-3-CO | piperidinyl-methyl-indoline | CH₂cHex | CONH₂ |
| 58 | 2-methylpyridine-3-CO | tetrahydroisoquinoline | 4-pyridyl-ethyl | H |
| 59 | 2-methylpyridine-3-CO | tetrahydroquinoline | 4-pyridyl-ethyl | CONH₂ |
| 60 | 2-methylpyridine-3-CO | tetrahydroisoquinoline | cHexCH₂ | H |
| 61 | 3-methylbenzoyl | tetrahydroisoquinoline | Bn | CONH₂ |
| 62 | 2-methylpyridine-3-CO | tetrahydroquinoline | nBu | CONH₂ |
| 63 | 2-methylpyridine-3-CO | tetrahydroquinoline | Bn | CONH₂ |
| 64 | 2-methylpyridine-3-CO | Me₂N-methyl-indoline | Bn | CONH₂ |
| 65 | 2-methylpyridine-3-CO | Et₂N-methyl-indoline | CH₂cHex | H |
| 66 | 2-methylpyridine-3-CO | morpholinyl-methyl-indoline | Bn | H |
| 67 | 2-methylpyridine-3-CO | N-methylpiperazinyl-methyl-indoline | CH₂cHex | H |
| 68 | 2-methylpyridine-3-CO | indoline | 3-ethylthiophene | CONH₂ |

-continued

| No. | (R¹)n—B—CO | A | R² | R³ |
|---|---|---|---|---|
| 69 | 2-methylpyridine-3-CO | 1,2,3,4-tetrahydroisoquinoline | nBu | CONH$_2$ |
| 70 | pyridine-3-CO | 1,2,3,4-tetrahydroquinoline | cHexCH$_2$ | H |
| 71 | 2-methylpyridine-3-CO | 1,2,3,4-tetrahydroisoquinoline | Bn | CONH-CH$_2$CH$_2$-(2-pyridyl) |
| 72 | 4-methylbenzoyl | 1,2,3,4-tetrahydroquinoline | Bn | H |
| 73 | 2-methylpyridine-3-CO | 6-(NEt$_2$-CH$_2$)-1,2,3,4-tetrahydroisoquinoline | Bn | CONH$_2$ |
| 74 | pyridine-3-CO | isoindoline | nBu | H |
| 75 | pyridine-3-CO | 6-(morpholinomethyl)-1,2,3,4-tetrahydroisoquinoline | Bn | H |
| 76 | 2-methylpyridine-3-CO | isoindoline | cHexCH$_2$ | CONH$_2$ |
| 77 | 2-methylpyridine-3-CO | 1,2,3,4-tetrahydroisoquinoline | Bn | CONH-CH$_2$CH$_2$-morpholine |
| 78 | 3-methylbenzoyl | 1,2,3,4-tetrahydroisoquinoline | Bn | H |
| 79 | 4-methylpyridine-3-CO | 6-OMe-1,2,3,4-tetrahydroisoquinoline | Bn | H |
| 80 | 4-methylpyridine-3-CO | 6-OMe-1,2,3,4-tetrahydroisoquinoline | Bn | CONH$_2$ |

-continued
| No. | (R¹)n—B—CO | A | R² | R³ |
|---|---|---|---|---|
| 81 | 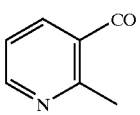 | 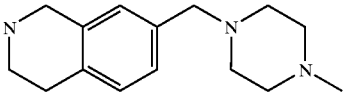 | Bn | H |
| 82 | 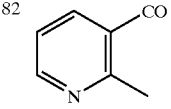 | 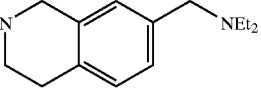 | nBu | H |
| 83 | 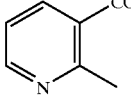 | 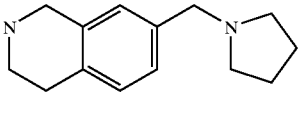 | Bn | CONH₂ |
| 84 | 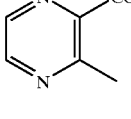 | 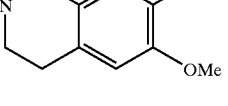 | Bn | CONH₂ |
| 85 | 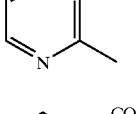 | 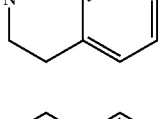 | nBu | H |
| 86 | 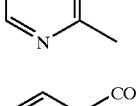 | 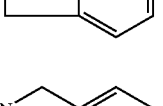 | Bn | CONH₂ |
| 87 | 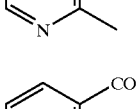 | 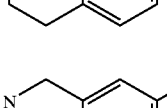 | cHexCH₂ | CONH₂ |
| 88 | 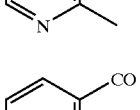 | 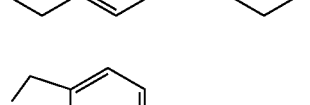 | Bn | CONH₂ |
| 89 | 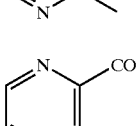 | 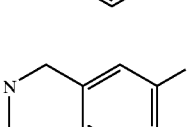 | cHexCH₂ | H |
| 90 | 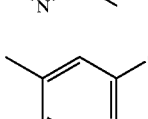 | 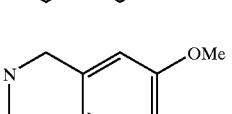 | Bn | H |
| 91 |  |  | Bn | CONH₂ |
| 92 | 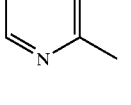 | 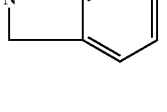 | Bn | H |

-continued
| No. | (R¹)n—B—CO | A | R² | R³ |
|---|---|---|---|---|
| 93 | 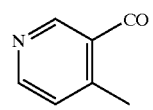 | 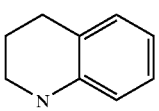 | Bn | H |
| 94 | 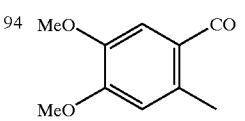 | 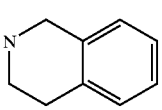 | Bn | CONH$_2$ |
| 95 | 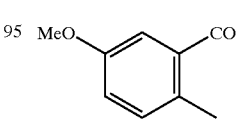 | 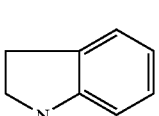 | Bn | CONH$_2$ |
| 96 | 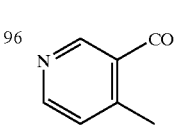 | 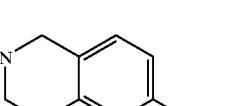 | Bn | H |
| 97 | 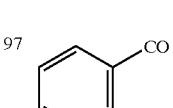 | 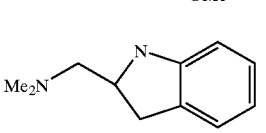 | Bn | H |
| 98 | 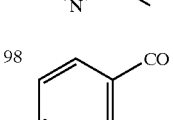 | 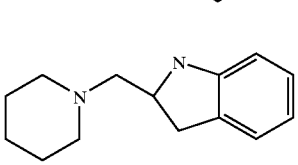 | nBu | CONH$_2$ |
| 99 | 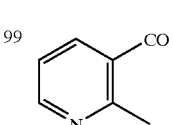 | 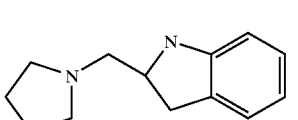 | CH$_2$cHex | CONH$_2$ |
| 100 | 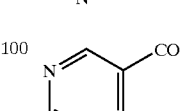 | 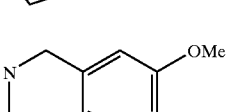 | Bn | CONH$_2$ |
| 101 | 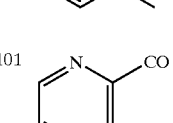 | 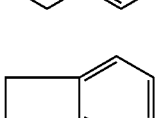 | Bn | H |
| 102 | 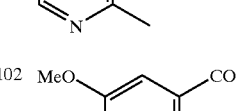 | 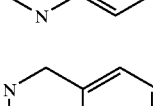 | Bn | CONH$_2$ |
| 103 | 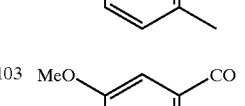 | 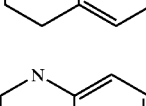 | Bn | H |
| 104 | 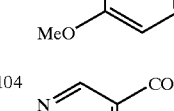 | 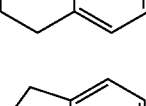 | Bn | CONH$_2$ |

-continued
| No. | (R¹)n—B—CO | A | R² | R³ |
|---|---|---|---|---|
| 105 | 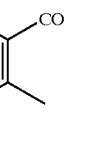 | 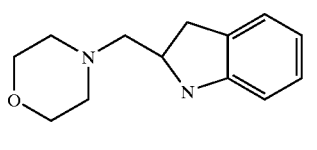 | Bn | $CONH_2$ |
| 106 | 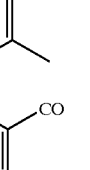 | 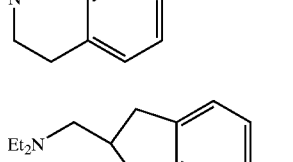 | Bn | $CONH_2$ |
| 107 | 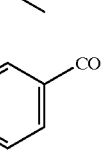 | 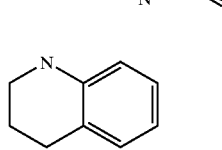 | Bn | $CONH_2$ |
| 108 | 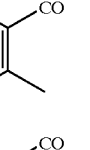 | 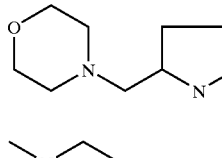 | Bn | H |
| 109 |  | 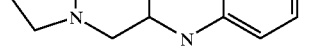 | nBu | $CONH_2$ |
| 110 | 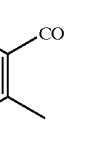 | 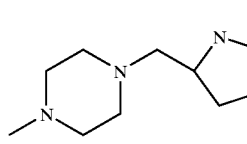 | $CH_2cHex$ | $CONH_2$ |
| 111 | 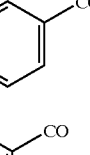 | 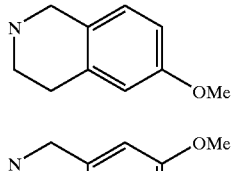 | $CH_2cHex$ | H |
| 112 | 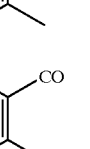 | 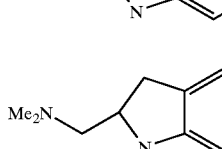 | Bn | H |
| 113 | 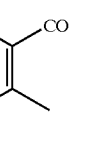 | 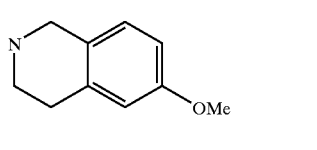 | nBu | $CONH_2$ |
| 114 | 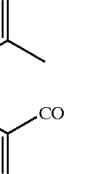 | 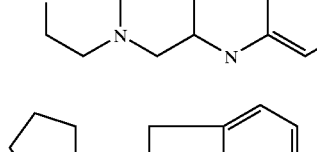 | $CH_2cHex$ | $CONH_2$ |
| 115 |  |  | nBu | $CONH_2$ |
| 116 |  |  | Bn | H |

-continued
| No. | (R¹)n—B—CO | A | R² | R³ |
|---|---|---|---|---|
| 117 | 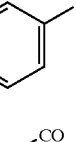 | 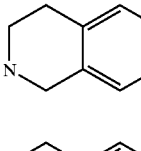 | Bn | H |
| 118 | 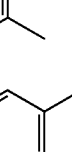 | 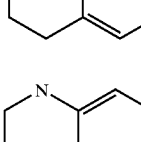 | Bn | H |
| 119 | 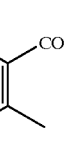 | 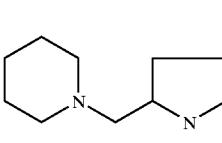 | Bn | CONH$_2$ |
| 120 | 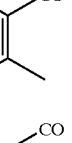 | 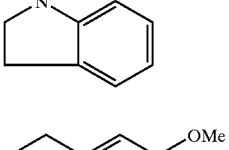 | nBu | CONH$_2$ |
| 121 |  | 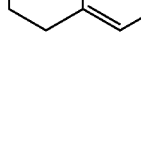 | nBu | H |
| 122 | 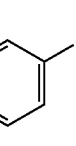 | 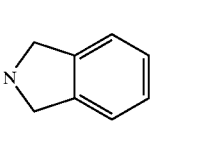 | Bn | CONH$_2$ |
| 123 | 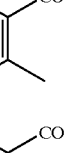 | 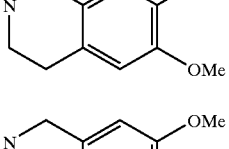 | Bn | CONH$_2$ |
| 124 | 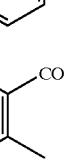 | 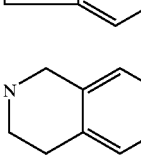 | nBu | H |
| 125 | 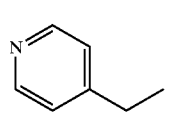 | 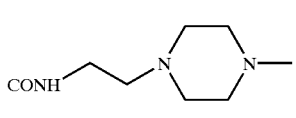 | 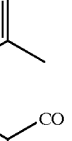 | 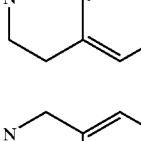 |
| 126 | 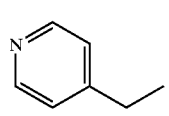 | 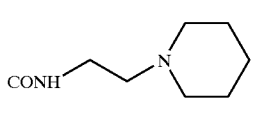 |  |  |
| 127 |  | | nBu | |
| 128 | | | Bu | H |

-continued

| No. | (R¹)n—B—CO | A | R² | R³ |
|---|---|---|---|---|
| 129 | 2-methylpyridin-3-yl-CO | 6-(NMe₂)-1,2,3,4-tetrahydroisoquinolin-2-yl | 3-ethylthiophen-2-yl | CONH-CH₂CH₂-(pyridin-2-yl) |
| 130 | 2-methylpyridin-3-yl-CO | 6-(CH₂NEt₂)-1,2,3,4-tetrahydroisoquinolin-2-yl | Bn | CONH₂ |
| 131 | 2-methylpyridin-3-yl-CO | 6-(piperidin-1-ylmethyl)-1,2,3,4-tetrahydroisoquinolin-2-yl | Bn | H |
| 132 | 2-methylpyridin-3-yl-CO | 6-(pyrrolidin-1-ylmethyl)-1,2,3,4-tetrahydroisoquinolin-2-yl | Bn | CONH₂ |
| 133 | 2-methylpyridin-3-yl-CO | 6-(piperidin-1-ylmethyl)-1,2,3,4-tetrahydroisoquinolin-2-yl | pyridin-4-ylmethyl | CONH-CH₂CH₂-(morpholin-4-yl) |
| 134 | 2-methylpyridin-3-yl-CO | 6-((4-methylpiperazin-1-yl)methyl)-1,2,3,4-tetrahydroisoquinolin-2-yl | Bn | CONH₂ |
| 135 | 2-methylphenyl-CO | 6,7-dimethoxy-1,2,3,4-tetrahydroisoquinolin-2-yl | Bn | CONH₂ |
| 136 | 4-methylphenyl-CO | 7-methoxy-1,2,3,4-tetrahydroisoquinolin-2-yl | Bn | CONH₂ |
| 137 | 2-methylpyridin-3-yl-CO | 1,2,3,4-tetrahydroisoquinolin-2-yl | 1H-indol-3-ylmethyl | H |
| 138 | 2-methylpyridin-3-yl-CO | 2,3-dihydroindol-1-yl | 1H-indol-3-ylmethyl | CONH₂ |
| 139 | 2-methylpyridin-3-yl-CO | 6-(morpholin-4-ylmethyl)-1,2,3,4-tetrahydroisoquinolin-2-yl | Bn | H |

-continued
| No. | (R¹)n—B—CO | A | R² | R³ |
|---|---|---|---|---|
| 140 |  | 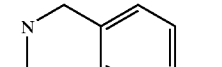 | Bn | H |
| 141 |  | 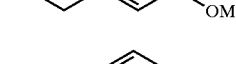 | Bn | H |
| 142 |  | 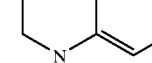 | Bn | 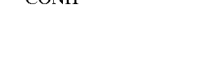 |
| 143 |  | 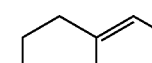 | Bn | 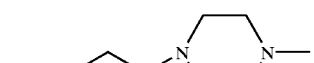 |
| 144 |  | 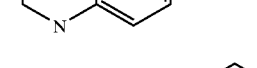 | Bn |  |
| 145 |  | 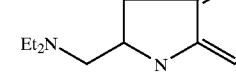 | nBu | H |
| 146 |  | 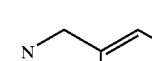 | nBu | CONH₂ |
| 147 |  | 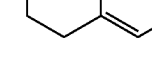 | Bn | H |
| 148 |  | 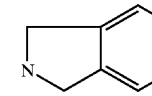 | Bn | CONH₂ |
| 149 |  |  | Bn | CONH₂ |
| 150 |  | 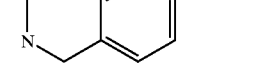 | CH₂cHex | H |
| 151 |  | 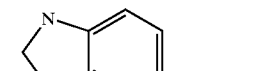 | Bn | CONH₂ |
| 152 |  | 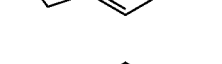 | nBu | H |

-continued

| No. | (R¹)n—B—CO | A | R² | R³ |
|---|---|---|---|---|
| 153 | 2-methylpyridine-3-CO | 6-(morpholinomethyl)-1,2,3,4-tetrahydroisoquinoline | CH₂cHex | CONH₂ |
| 154 | 2-methylpyridine-3-CO | 6-(piperidinomethyl)-1,2,3,4-tetrahydroisoquinoline | nBu | CONH₂ |
| 155 | 3-methylpyrazine-2-CO | 6,7-dimethoxy-1,2,3,4-tetrahydroisoquinoline | nBu | H |
| 156 | 2-methylpyridine-3-CO | indoline | nBu | CONH₂ |
| 157 | 2-methylbenzoyl | isoindoline | Bn | H |
| 158 | 2-methylbenzoyl | isoindoline | Bn | CONH₂ |
| 159 | 2-methylpyridine-3-CO | isoindoline | Bn | H |
| 160 | 2-methylpyridine-3-CO | 6-(pyrrolidinomethyl)-1,2,3,4-tetrahydroisoquinoline | CH₂cHex | H |
| 161 | 2-methylpyridine-3-CO | 6-((4-methylpiperazin-1-yl)methyl)-1,2,3,4-tetrahydroisoquinoline | Bn | CONH₂ |
| 162 | 3-methylpyrazine-2-CO | 6-methoxy-1,2,3,4-tetrahydroisoquinoline | nBu | H |
| 163 | 4-methylpyridine-3-CO | 6,7-dimethoxy-1,2,3,4-tetrahydroisoquinoline | nBu | CONH₂ |
| 164 | 2-methylpyridine-3-CO | 2-((dimethylamino)methyl)indoline | nBu | H |

-continued
| No. | (R¹)n—B—CO | A | R² | R³ |
|---|---|---|---|---|
| 165 | 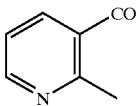 | 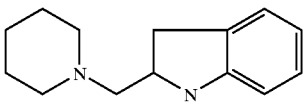 | $CH_2cHex$ | H |
| 166 | 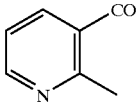 | 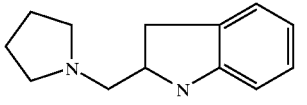 | Bn | $CONH_2$ |
| 167 | 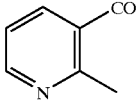 | 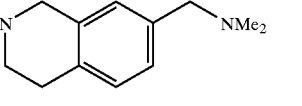 | nBu | $CONH_2$ |
| 168 | 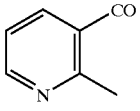 | 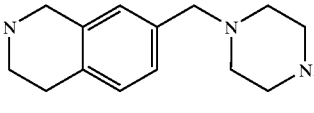 | nBu | H |
| 169 | 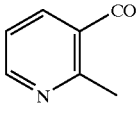 | 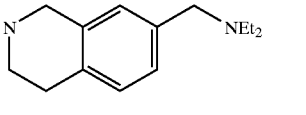 | $CH_2cHex$ | $CONH_2$ |
| 170 | 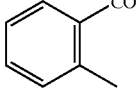 | 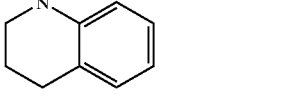 | Bn | $CONH_2$ |
| 171 | 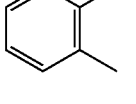 | 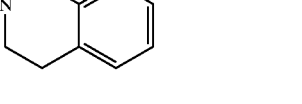 | Bn | H |
| 172 | 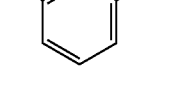 | 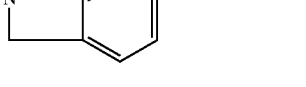 | Bn | $CONH_2$ |
| 173 | 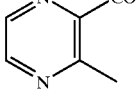 | 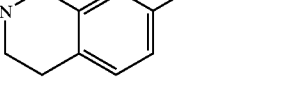 | nBu | $CONH_2$ |
| 174 | 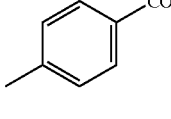 | 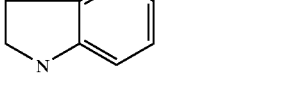 | Bn | H |
| 175 | 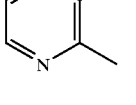 | 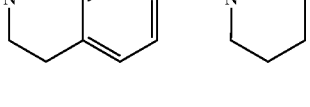 | $CH_2cHex$ | H |
| 176 | 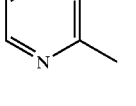 | 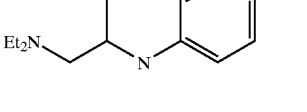 | Bn | $CONH_2$ |

-continued

| No. | (R¹)n—B—CO | A | R² | R³ |
|---|---|---|---|---|
| 177 | 2-methylpyridine-3-CO | morpholinomethyl-indoline | CH₂cHex | H |
| 178 | 2-methylpyridine-3-CO | piperazinylmethyl-indoline | Bn | H |
| 179 | 2-methylpyridine-3-CO | tetrahydroisoquinoline-pyrrolidinylmethyl | nBu | CONH₂ |
| 180 | 2-methylpyridine-3-CO | tetrahydroisoquinoline-morpholinomethyl | nBu | H |
| 181 | 2-methylpyridine-3-CO | tetrahydroquinoline | Bn | CONH-CH₂CH₂-(4-methylpiperazin-1-yl) |
| 182 | 3-methylpyrazine-2-CO | tetrahydroisoquinoline | Bn | CONH₂ |
| 183 | 4-methylpyridine-3-CO | indoline | Bn | H |
| 184 | 4,5-dimethoxy-2-methylbenzoyl | tetrahydroquinoline | Bn | CONH₂ |
| 185 | 4,5-dimethoxy-2-methylbenzoyl | isoindoline | Bn | CONH₂ |
| 186 | 4,5-dimethoxy-2-methylbenzoyl | isoindoline | CH₂cHex | CONH-CH₂CH₂-morpholino |
| 187 | 2-methylpyridine-3-CO | 5-(NEt₂-methyl)-indoline | Bn | CONH₂ |
| 188 | 2-methylpyridine-3-CO | 2-(NEt₂-methyl)-indoline | Bn | H |

-continued
| No. | (R¹)n—B—CO | A | R² | R³ |
|---|---|---|---|---|
| 189 | 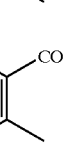 | 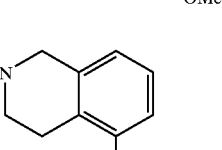 | nBu | H |
| 190 |  | 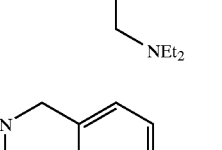 | nBu | $CONH_2$ |
| 191 | 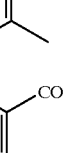 | 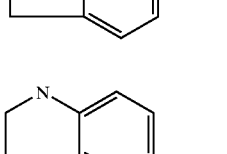 | Bn | H |
| 192 | 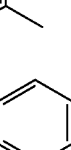 | 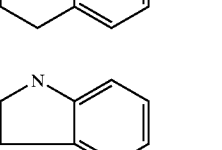 | Bn | H |
| 193 | 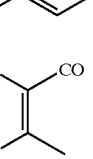 | 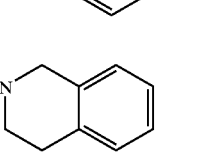 | Bn | $CONH_2$ |
| 194 | 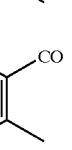 | 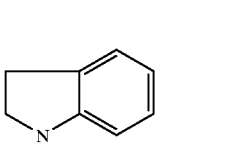 | Bn | $CONH_2$ |
| 195 | 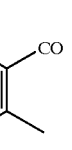 | 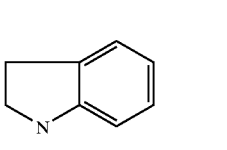 | Bn | H |
| 196 | 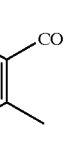 | 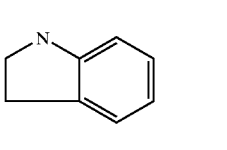 | Bn | $CONH_2$ |
| 197 | 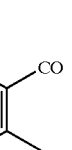 | 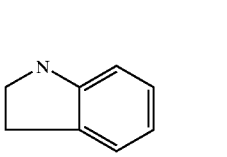 | Bn | H |
| 198 | 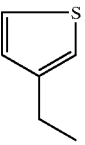 |  |  | H |
| 199 | 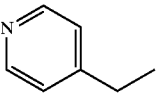 |  |  | H |

-continued
| No. | (R¹)n—B—CO | A | R² | R³ |
|---|---|---|---|---|
| 200 | 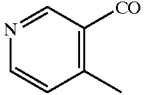 | 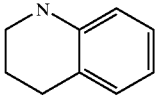 | 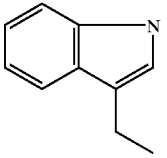 | 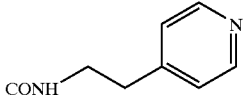 |
| 201 | 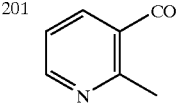 | 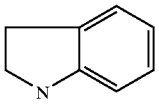 | nBu | H |
| 202 | 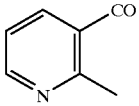 | 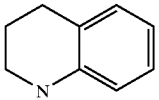 | Bn | H |
| 203 | 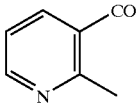 | 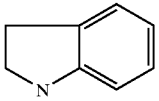 | cHexCH$_2$ | CONH$_2$ |
| 204 | 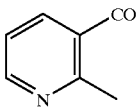 | 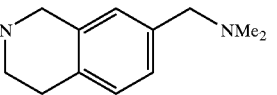 | cHexCH$_2$ | CONH$_2$ |
| 205 | 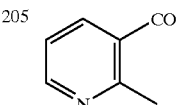 | 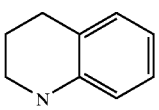 | nBu | H |
| 206 | 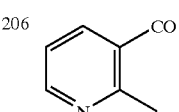 | 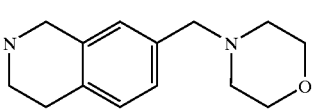 | nBu | CONH$_2$ |
| 207 | 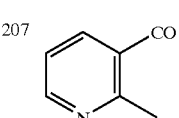 | 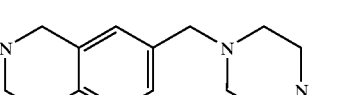 | cHexCH$_2$ | H |
| 208 | 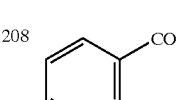 | 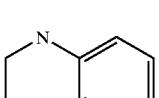 | 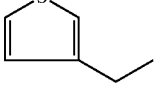 | CONH$_2$ |
| 209 | 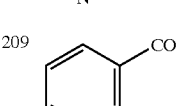 | 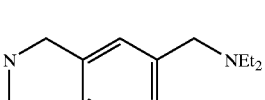 | Bn | H |
| 210 | 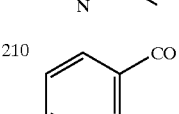 | 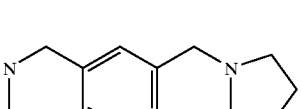 | nBu | H |
| 211 | 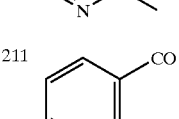 | 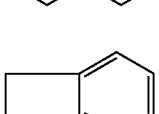 | Bn | H |

-continued
| No. | (R¹)n—B—CO | A | R² | R³ |
|---|---|---|---|---|
| 212 | 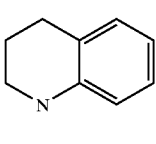 | 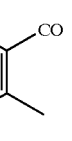 | cHexCH$_2$ | H |
| 213 | 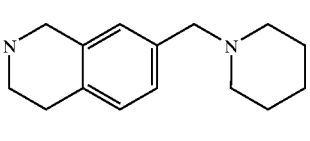 | 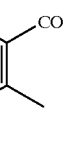 | cHexCH$_2$ | CONH$_2$ |
| 214 | 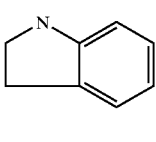 | 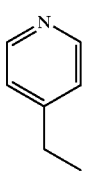 | Bn | H |
| 215 | 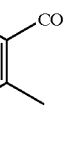 | 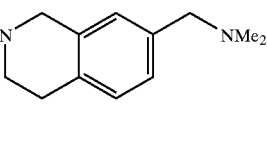 | cHexCH$_2$ | CONH$_2$ |
| 216 | 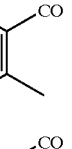 | 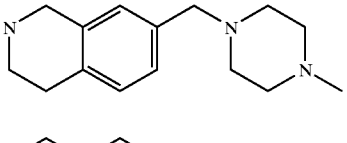 | 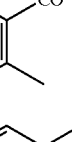 | CONH$_2$ |
| 217 | 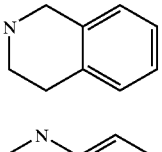 |  | Bn | H |
| 218 | 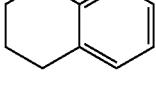 | 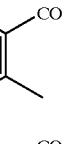 | cHexCH$_2$ | CONH$_2$ |
| 219 | 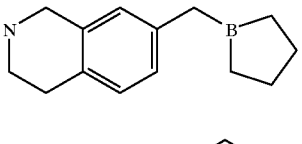 | 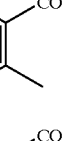 | Bn | CONH$_2$ |
| 220 | 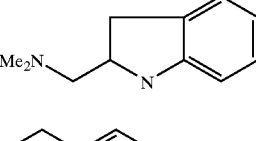 |  | Bn | CONH$_2$ |
| 221 | 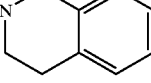 | 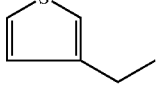 | cHexCH$_2$ | CONH$_2$ |
| 222 |  |  | cHexCH$_2$ | CONH$_2$ |
| 223 |  |  |  | H |

-continued

| No. | (R¹)n—B—CO | A | R² | R³ |
|---|---|---|---|---|
| 224 | 4-methylbenzoyl | indoline | Bn | $CONH_2$ |
| 225 | 2-methylpyridine-3-carbonyl | 1,2,3,4-tetrahydroquinoline | 3-ethylthiophen-2-yl | H |
| 226 | 2-methylpyridine-3-carbonyl | 2-(piperidin-1-ylmethyl)-1,2,3,4-tetrahydroquinoline | nBu | H |
| 227 | 2-methylpyridine-3-carbonyl | 2-(morpholin-4-ylmethyl)indoline | nBu | H |
| 228 | 2-methylpyridine-3-carbonyl | 2-(piperidin-1-ylmethyl)indoline | Bn | $CONH_2$ |
| 229 | 2-methylbenzoyl | indoline | Bn | H |
| 230 | 2-methylpyridine-3-carbonyl | 7-(diethylaminomethyl)-1,2,3,4-tetrahydroisoquinoline | nBu | $CONH_2$ |
| 231 | 2-methylpyridine-3-carbonyl | 7-(piperidin-1-ylmethyl)-1,2,3,4-tetrahydroisoquinoline | nBu | H |
| 232 | 2-methylpyridine-3-carbonyl | 2-(piperidin-1-ylmethyl)indoline | nBu | H |
| 233 | 2-methylpyridine-3-carbonyl | 7-(morpholin-4-ylmethyl)-1,2,3,4-tetrahydroisoquinoline | cHexCH₂ | H |
| 234 | 2-methylpyridine-3-carbonyl | indoline | Bn | CONH-CH₂CH₂-morpholine |
| 235 | 3-methylbenzoyl | 6,7-dimethoxy-1,2,3,4-tetrahydroisoquinoline | Bn | H |

-continued

| No. | (R¹)n—B—CO | A | R² | R³ |
|---|---|---|---|---|
| 236 | 4-methylbenzoyl | 6-methoxy-tetrahydroisoquinoline | Bn | $CONH_2$ |
| 237 | 4-methylbenzoyl | 6-methoxy-tetrahydroisoquinoline | Bn | $CONH$-ethyl-morpholine |
| 238 | 2-methylnicotinoyl | 6-($CH_2NEt_2$)-tetrahydroisoquinoline | Bn | H |
| 239 | 2-methylnicotinoyl | 6-($CH_2$-pyrrolidinyl)-tetrahydroisoquinoline | Bn | H |
| 240 | 2-methylnicotinoyl | 6-($CH_2$-morpholinyl)-tetrahydroisoquinoline | Bn | $CONH_2$ |
| 241 | 2-methylnicotinoyl | 6-($CH_2$-piperidinyl)-tetrahydroisoquinoline | Bn | $CONH_2$ |
| 242 | 2-methylbenzoyl | 7-methoxy-tetrahydroisoquinoline | Bn | H |
| 243 | 2-methylnicotinoyl | tetrahydroisoquinoline | 3-ethyl-indolyl | $CONH_2$ |
| 244 | 2-methylnicotinoyl | tetrahydroisoquinoline | 3-ethyl-indolyl | H |
| 245 | 2-methylbenzoyl | 6-methoxy-tetrahydroisoquinoline | Bn | $CONH$-ethyl-morpholine |
| 246 | 2-methylnicotinoyl | 6-($CH_2NMe_2$)-tetrahydroisoquinoline | Bn | $CONH_2$ |
| 247 | 2-methylnicotinoyl | 6-($CH_2$-N-methylpiperazinyl)-tetrahydroisoquinoline | Bn | H |

| No. | (R¹)n—B—CO | A | R² | R³ |
|---|---|---|---|---|
| 248 | 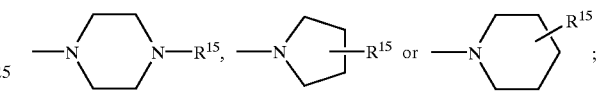 | indoline | cHexCH₂ | CONH-CH₂CH₂-NEt₂ |
| 249 | o-tolyl-CO | 6-methoxy-tetrahydroisoquinoline | Bn | H |
| 250 | p-tolyl-CO | 6,7-dimethoxy-tetrahydroisoquinoline | Bn | CONH₂ |

We claim:

1. A compound of formula I

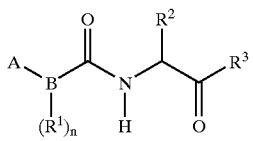

or a tautomeric or isomeric form, an enantiomeric or diastereomeric form, or a physiologically tolerated salt thereof, wherein A denotes a fused ring

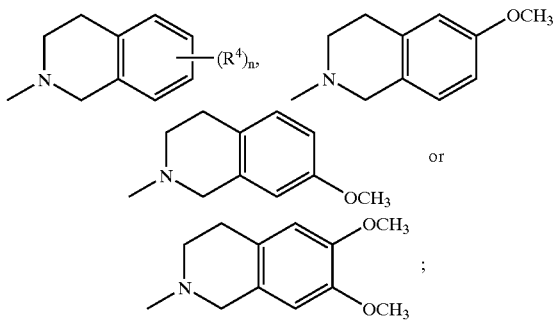

B is pyridyl;

$R^1$ is hydrogen, $C_1$–$C_6$-alkyl which is branched or unbranched, O—$C_1$–$C_6$-alkyl which is branched or unbranched, $C_2$–$C_6$-alkenyl, $C_2$–$C_6$-alkynyl, $C_1$–$C_6$-alkylphenyl, $C_2$–$C_6$-alkenylphenyl, $C_2$–$C_6$-alkynylphenyl, OH, Cl, F, Br, I, $CF_3$, $NO_2$, $NH_2$, CN, COOH, COO—$C_1$–$C_4$-alkyl, NHCO—$C_1$–$C_4$-alkyl, NHCO-phenyl, $CONHR^{11}$, $NHSO_2$—$C_1$–$C_4$-alkyl, $NHSO_2$-phenyl, $SO_2$—$C_1$–$C_4$-alkyl or $SO_2$-phenyl;

$R^2$ is $C_1$–$C_6$-alkyl which is branched or unbranched and which can additionally carry a phenyl, cyclohexyl, pyridyl, thienyl, indolyl or naphthyl ring which, for its part, is substituted by a maximum of two $R^1$ radicals;

$R^3$ is $COOR^5$ and CO-Z, in which

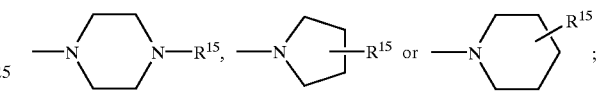

$R^4$ is hydrogen or $(CH_2)_m NR^8 R^9$, $O(CH_2)_m NR^8 R^9$ or

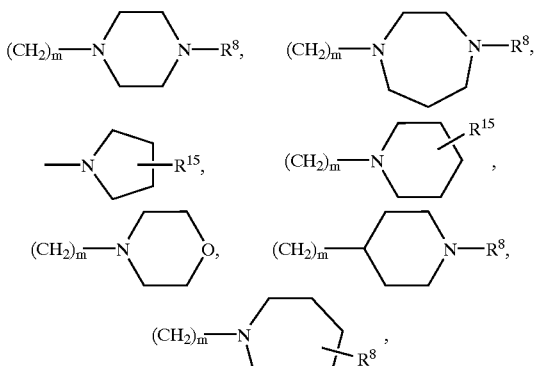

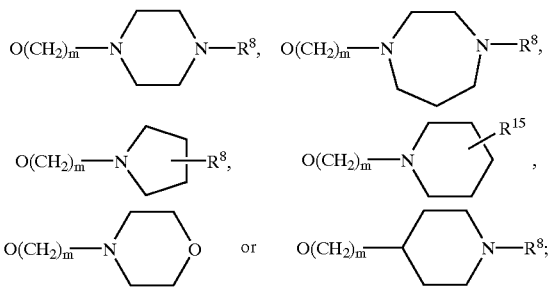

$R^5$ is $C_1$–$C_6$-alkyl which is straight-chain or branched and which can be substituted by a phenyl ring which can itself be additionally substituted by one or two $R^{10}$ radicals;

$R^6$ is hydrogen or $C_1$–$C_6$-alkyl which is branched or unbranched;

$R^7$ is hydrogen or $C_1$–$C_6$-alkyl which is branched or unbranched and which can additionally be substituted by a phenyl or pyridine ring, which can additionally carry an $R^{10}$ radical, or by

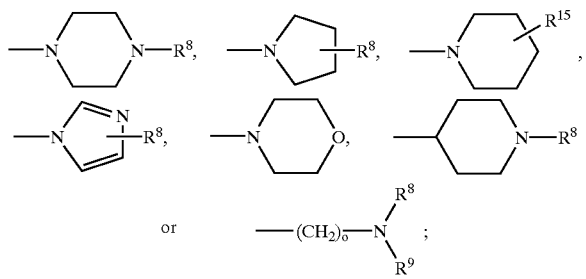

$R^8$ is $C_1-C_6$-alkyl which is straight-chain or branched and which can be substituted by a phenyl ring which can itself be additionally substituted by one or two $R^{10}$ radicals;

$R^9$ is $C_1-C_6$-alkyl which is straight-chain or branched and which can be substituted by a phenyl ring which can itself be additionally substituted by one or two $R^{10}$ radicals;

$R^{10}$ is hydrogen, $C_1-C_4$-alkyl which is branched or unbranched, —O—$C_1-C_4$-alkyl, OH, Cl, F, Br, I, $CF_3$, $NO_2$, $NH_2$, CN, $CONH_2$, COOH, COO—$C_1-C_4$-alkyl, —NHCO—$C_1-C_4$-alkyl, —NHCO-phenyl, —$NHSO_2$—$C_1-C_4$-alkyl, —$NHSO_2$-phenyl, —$SO_2$—$C_1-C_4$-alkyl or —$SO_2$-phenyl;

$R^{11}$ is hydrogen, $C_1-C_6$-alkyl which is branched or unbranched;

$R^{15}$ is hydrogen or has the meaning of $R^8$;

m is a number 1, 2, 3, 4, 5 or 6, and n is a number 0, 1 or 2, and o is a number 0, 1, 2, 3 or 4.

2. The compound of formula I defined in claim 1, wherein $R^3$ is $CONR^6R^7$.

3. The compound of formula I defined in claim 1, wherein $R^1$ is H.

4. The compound of formula I defined in claim 1, wherein $R^1$ is H, and $R^3$ is $CONH_2$.

5. A pharmaceutical preparation for peroral, parenteral and intraperitonal use, which comprises, per individual dose, an effective amount of at least one compound of formula I as defined in claim 1 in addition to the customary pharmaceutical adjuvants.

6. A method of inhibiting a cysteine protease in a subject requiring such inhibition which comprises administering an effective amount of the compound of formula I defined in claim 1.

7. The method of claim 6 wherein the inhibited cystein cysteine protease is a calpain or a cathepsin.

8. The method of claim 6 wherein the inhibited cystein cysteine protease is calpain I, calpain II, cathepsin B or cathepsin L.

9. The method of claim 6 wherein said subject exhibits a neurodegenerative disease or neuronal damage.

10. The method of claim 9 wherein the neurodegenerative disease or the neuronal damage is induced by ischemia, trauma or wide-spread hemorrhage.

11. The method of claim 6 wherein said subject suffers from stroke or craniocerebral trauma.

12. The method of claim 6 wherein said subject suffers from Alzheimer's disease or Huntington's disease.

13. The method of claim 6 wherein said subject suffers from epilepsy.

14. The method of claim 6 wherein said subject has suffered damage to the heart following cardiac ischemias, damage to the kidneys following renal ischemias, skeletal muscle damage, muscular dystrophies, a damage which arises from proliferation of the smooth muscle cells, coronary vasospasm, cerebral vasospasm, cataracts of the eyes or restenosis of the blood vessels following angioplasty.

15. The method of claim 6 wherein said subject has a tumor or a tumor and metastases.

16. The method of claim 6 wherein said subject has an elevated level of interleukin-1.

17. The method of claim 6 wherein said subject has an immunological disease.

18. The method of claim 7 wherein the immunological disease is an inflammation or a rheumatic disease.

* * * * *